United States Patent [19]

Sneer

[11] 4,051,598
[45] Oct. 4, 1977

[54] DENTAL IMPLANTS

[76] Inventor: Meer Sneer, 24 Baalei Melacha St., Tel-Aviv, Israel

[21] Appl. No.: 570,380

[22] Filed: Apr. 22, 1975

[30] Foreign Application Priority Data

Apr. 23, 1974  Israel .......................................... 44697

[51] Int. Cl.$^2$ ............................................ A61C 13/00
[52] U.S. Cl. .................................... 32/10 A; 128/92 C
[58] Field of Search ........... 32/10 A; 128/92 G, 92 B, 128/92 R

[56] References Cited

U.S. PATENT DOCUMENTS

| | | | |
|---|---|---|---|
| 3,787,900 | 1/1974 | McGee | 128/92 G |
| 3,789,029 | 1/1974 | Hodosh | 128/92 G |
| 3,808,606 | 5/1974 | Tronzo | 32/10 A |
| 3,827,145 | 8/1974 | Richards | 32/10 A |
| 3,828,772 | 8/1974 | Thiele | 128/92 G |
| 3,855,638 | 12/1974 | Pilliar | 32/10 A |
| 3,971,134 | 7/1976 | Bokros | 32/10 A |

Primary Examiner—Russell R. Kinsey
Assistant Examiner—Peter K. Skiff
Attorney, Agent, or Firm—Browdy and Neimark

[57] ABSTRACT

An endosseous dental implant comprising a lower part adapted to be inserted into the jawbone, having a surface-layer of open structure, containing a catalyst adapted to enhance osteogenesis. The surface layer is preferably porous and of about 100 to 400 $\mu$ thickness and the catalyst is preferably in granular form.

1 Claim, 4 Drawing Figures

DENTAL IMPLANTS

The present invention relates to a novel type of dental implant. It further relates to a novel process for the preparation of dental implants and to a process of dental implantation. Further aspects of the invention will become apparent hereinafter.

Hitherto various types of dental implants have been tried out on a great scale, and many varied shapes of implants have been tried out. Only partial success was attained, and this mainly due to the fact that the bond between the implant and the surrounding tissue was not a strong one, and thus implants tended to become loose after some time.

It is an object of the present invention to provide dental implants which form a strong and intimate bond with the surrounding tissue, a bond which is quite close to that of natural teeth. As will be set out hereinafter, various shapes of dental implants can be used according to the present invention, varying from a substantially exact copy of the shape of the lower part of the natural tooth removed by extraction, and to varying shapes, such as cones, screws and the like more.

Best results which can be attained depend on the individual case, and whether the implant replaces a recently removed tooth or whether it is inserted into a hole made in the jaw-bone.

When the dental implant is inserted into alveoles which remain after as extraction of a tooth shortly before the implantation, the best shape is a replica of the natural root shape. This is formed by casting an as exact replica as possible of the roots, with a suitable central body, resembling the extracted tooth.

When the dental implant is one implanted into a jaw bone wherein first a suitable hole is provided before implantation, the best shape is one of conical root shape, as per example described in my copending U.S. Patent Application No. 407,244, now U.S. Pat. No. 3,955,280.

In all the cases, the implant according to the invention is provided with a special surface layer of open structure, as will be described hereinafter, which contains a special catalyst enhancing natural osteogenesis.

The term "open structure" denotes a structure which comprises either a plurality of pores of certain pore size, a system of open channels or grooves or a combination of these. Advantageously there is provided a structure of interconnected pores and/or channels or surface grooves into which the bone can grow, thus resulting in a biological entity which is firmly anchored in the jaw bone.

The pores, grooves and channels are advantageously of a size of about 50 $\mu$ to about 250 $\mu$, and good results were obtained with an open sponge type structure.

The outer layer of the implant is of this open structure, and the outer layer is of about 100 to 200 $\mu$ thickness. Into the material of this open structure there is incorporated during the process of preparation a catalyst adapted to induce and enhance osteogenesis, so as to enlarge esteoblastosis, so as to enhance the invasion of the growing bone into the voids and channels of the structure. The area of contact between the implant and the surroundings is thus substantially increases, and a firm ultimate structure is attained. Due to the provision of this type of open structure, the surface area is enlarged by a factor of at least about 2, as compared with the area of contact of a natural tooth with the surrounding tissue. The open structure of the outer layer of the implant can be designated as "spongious structure", as "tunneled structure" or a "grooved structure". Grooved structures with grooves of about up to 400 $\mu$ width were found to be suitable. The minimum size of the pores, grooves and/or channels is one which makes possible the invasion of the bone cells, and practically a minimum size of about 50 $\mu$ was found suitable.

The catalyst is used in the shape of fine granules, and these are digested by the growing bone. The catalyst granules are incorporated into the material from which the surface layer is made, and these are advantageously of the order of about 50 to 100 $\mu$ particle size. It is possible to incorporate the catalyst also into the solid core of the implant, and for certain processes of manufacture of the implant, this is more convenient.

As material of construction of the implant there may be used one material, or there may be used a combination of various materials. Good results were obtained with certain physiologically acceptable plastics, such as methyl methacrylate and similar plastics, with epoxy resins and the like, with ceramic materials such as alumina, cesium-alumina, titanium sponge etc. In all the cases there is provided a solid core, covered at its lower part (the root of the implant) with a porous layer or with a channel structure.

When the implant is inserted into its place (either into the alveoles after extraction or into a hole drilled in the bone), the implant is first immobilized for a certain period of time (of a few weeks and up to 3–4 months) by connection with a vicinal tooth, by means of a common filling or by means of plastic material bridging the implant and one or two adjacent teeth. When the implant has become firmly bonded with its surroundings, the bond to the adjoining tooth or teeth is removed.

Experiments were carried out with a number of patients, and these are groupd into two groups:
  a. Extraction of a tooth, and insertion of a replacement implant;
  b. For edentation cases — a suitable hole is drilled into the jaw bone, and an implant is inserted.

In case (a) the tooth is extracted as carefully as possible, and when this is extracted without breakage of the roots, there is immediately formed a replica by casting a suitable material. If the roots are broken, the tooth is first reconstructed, and after this a replica is formed. The form of the roots is as similar to that of the natural roots as possible. This is easily accomplished by preparing a cast of silicon rubber or from alginote. A suitable material is cast into this form so as to obtain an exact replica of the natural tooth, especially as regard its lower part. The composition is cast in such manner as to obtain an "open structure" as defined above, and amongst others this may be accomplishd by greasing the interior of the cast, introducing into it some granules of suitable particle size of a water soluble salt (such as table salt, and casting into the thus produced cast the mixture containing the catalyst).

In case (b), there is used advantageously a cone-shaped root of the implant, as this shape has the best characteristics. An implant with more than one conical roots can be used. The conical lower part of the implant is advantageously provided with a plurality (2 or more) lateral protrusions which help to anchor the implant in place in the jaw bone. The conical member is provided with an open structure (pores, grooves or channels) as described above. The lower part of the implant serves as root, and this serves as support for the crown or for similar dental structures. If desired, shock absorber means are provided between the lower (root) and upper (crown) part of the implant. This can be in the form of a thin layer of elastic polymer, firmly bonded between the upper and lower parts of the implant. The lower part may be of any suitable material, for example, of a polymer such as a methyl-methacrylate, a ceramic, or suitable metal, whereas the upper part can be of a suitable metal, such as stainless steel, gold or the like. Suitable elastic polymers serving as shock absorber are silicone rubber and the like.

Various forms of dental implants have been described, and some novel implants were described in my copending patent applications. The novel implant, comprising an open structure on its lower part adapted to be inserted into the jaw bone in combination with a catalyst system, is applicable to all of these. It is clear that best results are obtained with implants having an optimum shape which ought to be as similar as possible to the natural form of the replaced tooth.

The present invention is illustrated with reference to the enclosed schematical drawing, in which.

Figure 1:
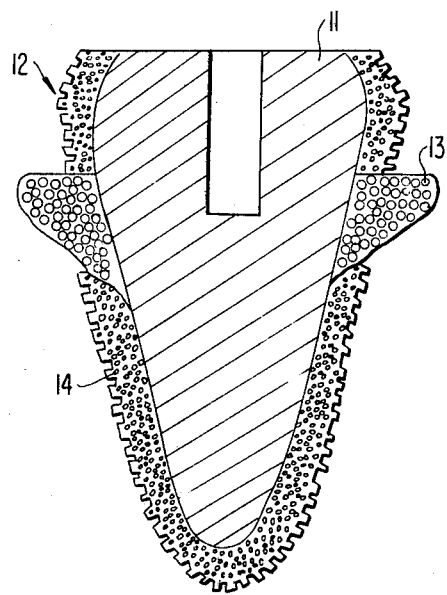
FIG. 1 is a side view, in partial section, of an implant which simulates the shape of the natural root of the tooth.

As shown in the Figures, the implant comprises a solid core 11, which is covered with a surface layer 12 of open structure. In FIG. 1 an open sponge-like structure is illustrated, comprising a plurality of interconnected pores 13 of about 100 to 300 μ. The layer 12 of the open structure is of about 0.2 mm to 0.4 mm thick.

In this outer layer 12, there are incorporated a multitude of grains of catalytically active substance 14.

Figure 2:
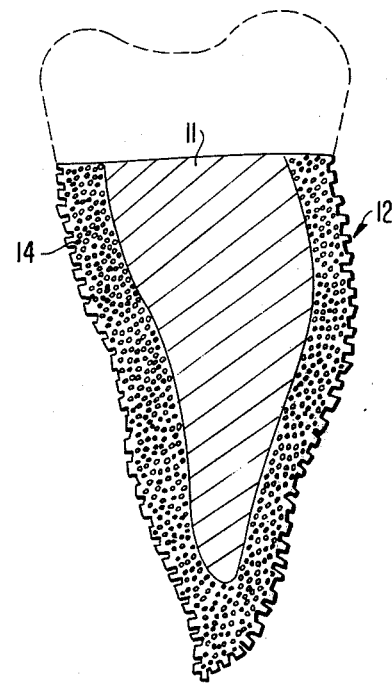
FIG. 2 is a side view, in partial section, of a standard conical implant.

In FIG. 2 a structure with a channel type structure is shown, which contains grains of catalytically active substance 14.

Figure 3:
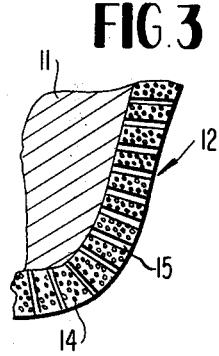
FIG. 3 is a sectional view through a part of an implant illustrating a different structure of the surface layer

As shown in FIG. 3, the implant comprises a solid core 11, a surface layer 12 containing a plurality of granulated catalyst particles 14, said layer 12 comprising a plurality of narrow grooves 15, extending around the root of the implant.

Figure 4:
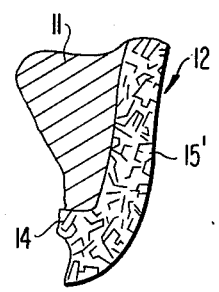
FIG. 4 is yet another partial section through root of an implant, illustrating a different embodiment of surface layer according to the invention.

As shown in FIG. 4, the lower part of the implant comprises a solid core 11, an outer layer 12 containing a plurality of catalyst granules 14, said layer 12 comprising a plurality of interconnected channels 15.

Various catalysts were tested and found to be effective. In the followng a number of representative examples of catalytic compositions is given. The catalytic mixtures were brought to granular form as is well known in the art, and grains of about 40 to 100 μ are a preferable size.

| Example 1: | | |
|---|---|---|
| Calcium carbonate | 0.5 | g |
| Tricalcium phosphate | 0.2 | g |
| Granulation excipient | up to 100 g | |
| Example 2: | | |
| Calcium fluoride | 0.4 | g |
| Calcium lactose | 20 | g |
| Excipient up to | 100 | g |
| Example 3: | | |
| Tribasic calcium phosphate | 10 | g |
| Excipient up to | 100 | g |
| Example 4: | | |
| Monobasic calcium phosphate | 10 | g |
| Excipient up to | 100 | g |
| Example 5: | | |
| Calcium glycerophosphate | 10 | g |
| Excipient up to | 1000 | g |
| Example 6: | | |
| Calcium lacticum | 02 | g |
| Starch | 2.5 | g |
| Excipient up to | 10.0 | g |
| Example 7: | | |
| Sodium fluoride | 1g of 1% solution | |
| Excipient up to | 1000 | g |
| Example 8: | | |
| Total bone substance (52% mineral, 42% organic) | 80 | g |
| Excipient up to | 100 | g |
| Example 9: | | |
| Total bone substance | 80 | g |
| Vitamin D | 3000 | i.u. |
| Excipient up to | 100 | g |
| Example 10: | | |
| Total Bone substance | 80 | g |
| Methyl testosterone | 5 | g |
| Granulation excipient up to | 100 | g |
| Example 11: | | |
| Magnessum silicate | 20 | g |
| Calcium carbonate | 20 | g |
| Aluminum silicate | 10 | g |
| Granulation excipient up to | 100 | g |
| Example 12: | | |
| Ascorbic acid | 50 | mg |
| Starch | 10 | g |
| Granulation excipient up to | 100 | g |
| Example 13: | | |
| Vitamin A | 10,000 | i.u. |
| Starch | 10 | g |
| Granulation excipient up to | 100 | g |
| Example 14: | | |
| Animal dentin | 40 | g |
| Granulation excipient | up to 100 g | |
| Example 15: | | |
| Dibasic calcium phosphate, pulvis | 10 | g |
| Granulation excipient up to | 100 | g |
| Example 16: | | |
| Calcium glucosicum | 3 | g |
| Calcium hexaphosphate | 7 | g |
| Granulation excipient up to | 100 | g |
| Example 17: | | |
| Magnesium silicate | 17.5 | g |
| Calcium carbonate | 17.5 | g |
| Aluminum silicate | 17.5 | g |
| Granulation excipient up to | 100 | g |
| Example 18: | | |
| Magnesium silicate | 17 | g |
| Calcium carbonate | 17 | g |
| Animal dentin | 17 | g |
| Granulation excipient up to | 100 | g |
| Example 19: | | |
| Total bone substance, mineral part 95% | 80 | g |
| Caoline | 10 | g |
| Zinc oxide | 10 | g |

Conventional physiologically acceptable granulation excipients are used, such as starch, methyl cellulose, gelatine, shallac, glucose or the like, or mixtures of any of these.

In all of the examples the catalyst is granulated to the desired particle size and these are incorporated into the material from which the dental implant is prepared. It can be incorporated into the entire mass of the lower part of the implant, or it can be incorporated into the surface layer of the root part of same.

For use as dental implants in the case of edentation, a variety of conus shaped members can be prepared, and the size and shape is chosed according to the individual case. These can be provided with an open porous layer or with a plurality of grooves or channels, which enable the bone tissue to grow into the surface layer and form an integral part therewith.

I claim:

1. An endosseous dental implant comprising a lower part, adapted to be inserted into the jaw bone, and having a surface layer 100 to 400 μ thick and of open structure comprising pores or interconnected channels of size of about 50 to about 250 μ, said surface layer being formed predominantly of a mixture of physiologically acceptable plastic and an osteogenesis enhancing catalyst selected from the group consisting of calcium carbonate, tricalcium phosphate, calcium fluoride, tribasic calcium phosphate, monobasic calcium phosphate, calcium glycero-phosphate, calcium lacticum, sodium fluoride, total bone substance, magnesium silicate, aluminum silicate, ascorbic acid, vitamin D, vitamin A, animal dentin, dibasic calcium phosphate, calcium glucosicum, calcium hexaphosphate, caoline, zinc oxide and mixtures thereof.

* * * * *